(12) United States Patent
Peine

(10) Patent No.: US 11,413,105 B2
(45) Date of Patent: *Aug. 16, 2022

(54) INPUT DEVICE ASSEMBLIES FOR ROBOTIC SURGICAL SYSTEMS

(71) Applicant: Covidien LP, Mansfield, MA (US)

(72) Inventor: William Peine, Ashland, MA (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/794,680

(22) Filed: Feb. 19, 2020

(65) Prior Publication Data
US 2020/0179071 A1   Jun. 11, 2020

Related U.S. Application Data

(63) Continuation of application No. 15/561,363, filed as application No. PCT/US2016/023519 on Mar. 22, 2016, now Pat. No. 10,582,979.
(Continued)

(51) Int. Cl.
*B25J 13/00* (2006.01)
*A61B 34/00* (2016.01)
(Continued)

(52) U.S. Cl.
CPC .............. *A61B 34/74* (2016.02); *A61B 34/35* (2016.02); *A61B 34/37* (2016.02); *A61B 34/76* (2016.02);
(Continued)

(58) Field of Classification Search
CPC ......... A61B 34/74; A61B 34/76; A61B 34/77; A61B 34/35; A61B 34/37;
(Continued)

(56) References Cited

U.S. PATENT DOCUMENTS 6,459,926 B1   10/2002   Nowlin et al.
6,793,653 B2   9/2004   Sanchez et al.
(Continued)

FOREIGN PATENT DOCUMENTS

JP   H0871072 A   3/1996
JP   08224245   9/1996
(Continued)

OTHER PUBLICATIONS

Order of Magnitdue Physics Mar. 20, 2006 (Year: 2006).*
(Continued)

*Primary Examiner* — Ian Jen

(57) ABSTRACT

Methods and devices for controlling a robotic system includes receiving a signal in response to movement of an input device through an input distance, determining the position of a repositioning control disposed on the input device, and moving the tool of the robotic system in response to movement of the input device the input distance. The input device is coupled to an input shaft of an input arm. The robotic system moving the tool a first distance when the repositioning control is in a deactivated position and moves the tool a second distance when the repositioning control in an activated position. The first distance is greater than the second distance.

18 Claims, 5 Drawing Sheets

Related U.S. Application Data

(60) Provisional application No. 62/138,432, filed on Mar. 26, 2015.

(51) Int. Cl.
| | | |
|---|---|---|
| *A61B 34/35* | (2016.01) | |
| *A61B 34/37* | (2016.01) | |
| *B25J 9/16* | (2006.01) | |
| *A61B 17/00* | (2006.01) | |

(52) U.S. Cl.
CPC ............ *A61B 34/77* (2016.02); *B25J 9/1674* (2013.01); *B25J 9/1689* (2013.01); *B25J 13/00* (2013.01); *A61B 2017/00477* (2013.01); *G05B 2219/45119* (2013.01)

(58) Field of Classification Search
CPC ......... A61B 2017/00477; B25J 9/1689; G05B 2219/45119
See application file for complete search history.

(56) References Cited

U.S. PATENT DOCUMENTS

| | | | |
|---|---|---|---|
| 7,391,177 B2 | 6/2008 | Kishi et al. | |
| 7,695,481 B2 | 4/2010 | Wang et al. | |
| 8,002,767 B2 | 8/2011 | Sanchez | |
| 9,671,860 B2 | 6/2017 | Ogawa et al. | |
| 10,582,979 B2 | 3/2020 | Peine | |
| 2002/0128552 A1* | 9/2002 | Nowlin ............... | A61B 34/35 600/427 |
| 2007/0083098 A1 | 4/2007 | Stern et al. | |
| 2008/0215065 A1* | 9/2008 | Wang .................. | A61B 34/70 606/130 |
| 2011/0301616 A1 | 12/2011 | Sanchez et al. | |
| 2012/0116416 A1 | 5/2012 | Neff et al. | |
| 2012/0283745 A1 | 11/2012 | Goldberg | |
| 2015/0045812 A1 | 2/2015 | Seo | |
| 2018/0014897 A1 | 1/2018 | Peine | |

FOREIGN PATENT DOCUMENTS

| | | | |
|---|---|---|---|
| JP | 2005511334 A | 4/2005 | |
| JP | 2013035117 A | 2/2013 | |
| WO | 2014136583 A1 | 9/2014 | |
| WO | 2015012241 A1 | 1/2015 | |

OTHER PUBLICATIONS

Japanese Office Action for application No. 2017-545711 dated Aug. 17, 2020 with English translation.
Chinese Second Office Action dated Jun. 2, 2020 corresponding to counterpart Patent Application CN 201680030390.4.
Australian Examination Report No. 1 dated May 13, 2020 corresponding to counterpart Patent Application AU 2016235358.
Indian First Examination Report dated Jul. 8, 2020 corresponding to counterpart Patent Application IN 201717030217.
Japanese Office Action dated Dec. 27, 2019 corresponding to counterpart Patent Application JP 2017-545711.
International Search Report for (PCT/US2016/023519) date of completion is Jul. 21, 2016 (six (6) pages).
European Search Report dated Oct. 2, 2018 issued in EP 16769533.
Japanese Office Action issued in corresponding Japanese Application No. 2017-545711 dated Jan. 20, 2021, 6 pages.
Chinese Office Action for application No. 201680030390.4 dated Jan. 4, 2021 with English translation.
Chinese Fourth Office Action dated Apr. 27, 2021 corresponding to counterpart Patent Application CN 201680030390.4.
Chinese Decision of Rejection dated Aug. 20, 2021 corresponding to counterpart Patent Application CN 201680030390.4.

* cited by examiner

INPUT DEVICE ASSEMBLIES FOR ROBOTIC SURGICAL SYSTEMS

CROSS-REFERENCE TO RELATED APPLICATIONS

This application is a Continuation Application which claims the benefit of and priority to U.S. patent application Ser. No. 15/561,363, filed on Sep. 25, 2017, which is a U.S. National Stage Application filed under 35 U.S.C. § 371(a) of International Patent Application No. PCT/US2016/023519, filed Mar. 22, 2016, which claims the benefit of and priority to U.S. Provisional Patent Application No. 62/138,432, filed Mar. 26, 2015, the entire disclosure of each of which being incorporated by reference herein.

BACKGROUND

Robotic surgical systems have been used in minimally invasive medical procedures. During such a medical procedure, the robotic surgical system is controlled by a surgeon interfacing with a user interface. The user interface allows the surgeon to manipulate an end effector that acts on a patient. The user interface includes an input controller or handle that is moveable by the surgeon to control the robotic surgical system.

Robotic surgical systems typically use a scaling factor to scale down the motions of the surgeons hands to determine the desired position of the end effector within the patient so that the surgeon can more precisely move the end effector inside the patient. Since the input device handle has a fixed range of motion, for larger scaling factors the surgeon may reach an end of the range of motion of an input handle more often. The surgeon then has to "clutch" the handle to decouple the motion of the input handles from the end effector so that the surgeon could move the handles to a new position within the workspace of the user interface away from the end of the range of motion while the instruments remain stationary. Once the input handle was moved sufficiently away from the end of the range of motion, the surgeon "reclutches" the input handle with the end effector to recouple the motion of the input handle to motion of the end effector to complete the desired movement of the end effector. Typically, a foot pedal is used as to "clutch" the input handle. This communicative decoupling between the motion of the input handles from the end effector, if not managed properly, may raise safety issues during the "clutching" window when the communicative decoupling occurs. Additionally, during some procedures it may be desirable to enable fine movement of the end effector during the repositioning of the handles so that the end effector does not remain stationary and more susceptible to collisions with other moving body parts or instruments while the input device handles are being repositioned.

There is a need for a robotic surgical system having an input device handle that can be easily repositioned without requiring traditional "clutching" that keeps the end effector stationary and/or communicatively decoupled from the input device during the repositioning.

SUMMARY

In an aspect of the present disclosure, a method of controlling a tool of a robotic system includes receiving a signal representative of a movement distance of an input device that is coupled to an input shaft of an input arm, determining a state of an input device repositioning control, scaling the movement distance based on a repositioning scaling factor or an operating scaling factor depending on the state of the repositioning control, and moving the tool of the robotic system based on the scaled movement distance. The tool moves at least a non-zero order of magnitude lesser distance when the movement distance is scaled based on the repositioning scaling factor instead of the operating scaling factor. The method may include scaling the movement distance based on the repositioning scaling factor when the repositioning control is in an active state and scaling the movement distance based on the operating scaling factor when the repositioning control is in an inactive state.

In aspects, the repositioning control includes a ring disposed about the body of the input device. The method may include determining that the ring is in the active state when the ring is slid away from a neutral position along a longitudinal axis of the body of the input device and determining that the ring is in the inactive state when the ring is in the neutral position. The ring is slid distally along the longitudinal axis of the body.

In some aspects, the method includes determining that the ring is in the active state when the ring is rotated away from a neutral position about a longitudinal axis of the body of the input device and determining that the ring is in the inactive state when the ring is in the neutral position.

In certain aspects, the repositioning control of the input device includes a petal that extends radially from the body. The method may include determining that the petal is in the active state when the petal is moved away from a neutral position and determining that the ring is in the inactive state when the ring is in the neutral position. Engaging the petal of the input device may include pivoting the petal proximally. The petal may be moved away from the neutral position when pivoted away from the neutral position.

In particular aspects, the repositioning scaling factor is less than 1000. The repositioning scaling factor may be at least 50 when the operating scaling factor is between 1 and 5. The repositioning scaling factor may be between 100 and 500 and the operating scaling factor is not greater than 10. The repositioning scaling factor may be at least 50 and the operating scaling factor is selectable between a plurality of values.

In another aspect of the present disclosure, a robotic surgical system includes a processing unit, a robotic system, and a user interface. The robotic system includes a robot base, a linkage, and a tool. The linkage extends from the robot base and has a plurality of members that are configured to move in response to a scaled signal from the processing unit. The tool is supported at an end of the linkage. The user interface includes an input arm that has an input shaft. The user interface also includes an input device that is coupled to the input shaft. The input device includes a repositioning control that is in communication with the processing unit to selectively vary a scaling factor of movement of the input shaft to movement of the tool.

In aspects, the repositioning control has an activated position such that movement of the input shaft is scaled by a first scaling factor to movement of the tool and a deactivated position such that movement of the input shaft is scaled by a second scaling factor to movement of the tool. The second scaling factor is different from the first scaling factor. The repositioning control may include a ring that is disposed about a body of the input device. The ring of the repositioning control may be slidable along or rotatable about a longitudinal axis of the body between activated and deactivated positions.

In some aspects, the repositioning control includes a petal that radially extends from the body of the input device. The petal may be pivotable proximally or distally from a deactivated position to an activated position.

In another aspect of the present disclosure, an input device for a robotic surgical system includes a body, a repositioning control, and a controller. The body is configured to couple to an input shaft of an input arm. The repositioning control is disposed on the body and is moveable between activated and deactivated positions. The controller is configured to transmit a signal to a processing unit to selectively vary a scaling factor of movement of the body to movement of a tool of the robotic surgical system. The repositioning control may be a ring slidable along a longitudinal axis of the body or a pivotable petal that extends radially from the body.

Further details and aspects of exemplary embodiments of the present disclosure are described in more detail below with reference to the appended figures.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
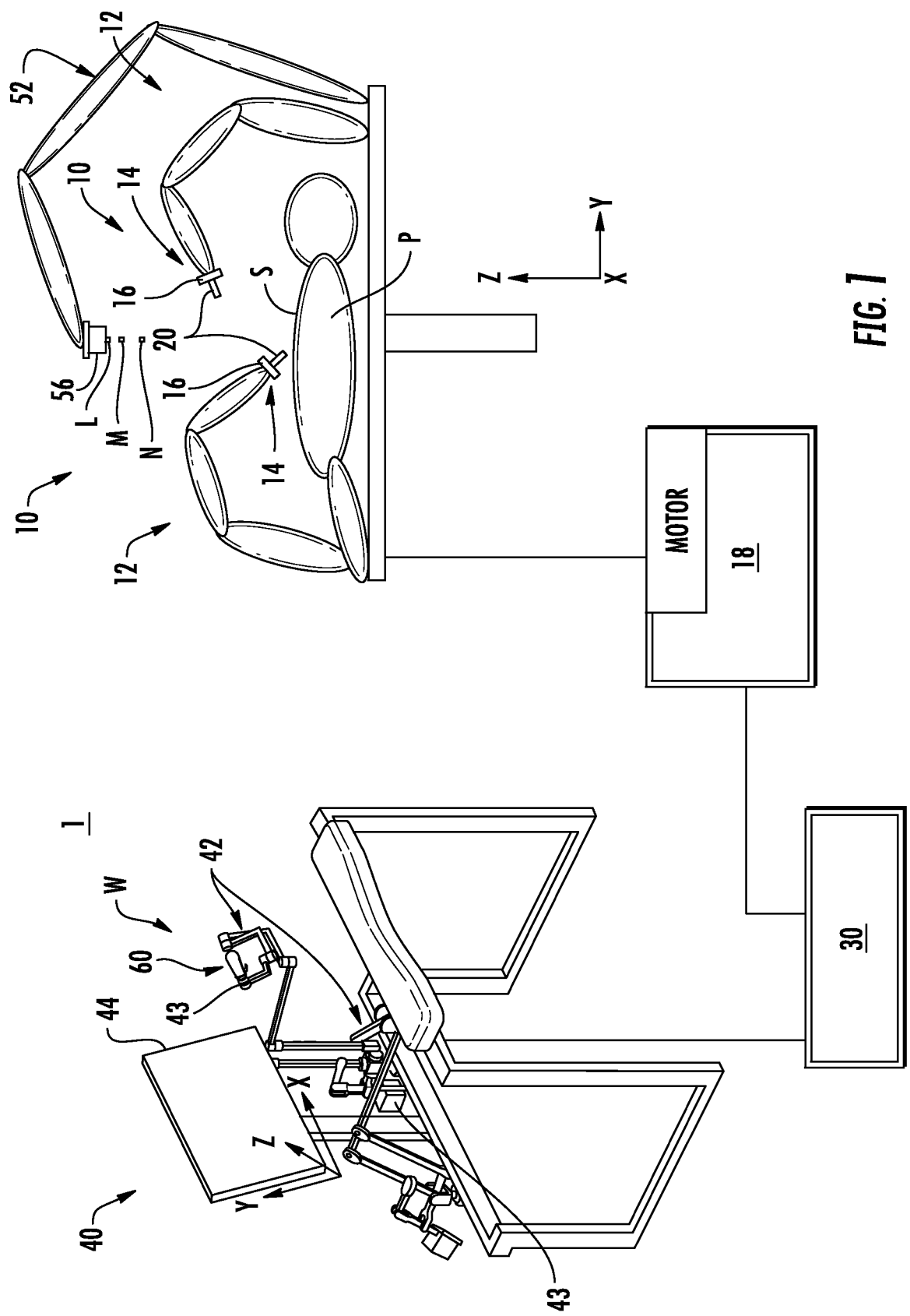
FIG. 1 is a schematic illustration of a robotic surgical system in accordance with the present disclosure including a user interface and a robotic system.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Some embodiments include a control for applying a repositioning scaling factor to a movement of the input device resulting in less movement of a tool coupled to a robotic arm linkage when the input device is moved. The lesser movement enables the input device to be repositioned relative to the tool while still leaving the input device operatively coupled to the tool. When the input device is repositioned, the repositioning scaling factor may be changed back to an operating scaling factor used during the surgical procedure resulting in greater movement of a tool coupled to a robotic arm linkage. This greater movement enables the clinician operating the input device to complete the surgical procedure in an efficient manner. The operating scaling factor may also be changed by the clinician during the surgical procedure to enable finer or coarser movements of the tool coupled to the input device.

Referring to FIG. 1, a robotic surgical system 1 in accordance with the present disclosure is shown generally as a robotic system 10, a processing unit 30, and a user interface 40. The robotic system 10 generally includes linkages 12 and a robot base 18. The linkages 12 moveably support an end effector or tool 20 which is configured to act on tissue. The linkages 12 may be in the form of arms each having an end 14 that supports an end effector or tool 20 which is configured to act on tissue. In addition, the ends 14 of the linkages 12 may include an imaging device 16 for imaging a surgical site "S". The user interface 40 is in communication with robot base 18 through the processing unit 30.

The user interface 40 includes a display device 44 which is configured to display three-dimensional images. The display device 44 displays three-dimensional images of the surgical site "S" which may include data captured by imaging devices 16 positioned on the ends 14 of the linkages 12 and/or include data captured by imaging devices that are positioned about the surgical theater (e.g., an imaging device positioned within the surgical site "S", an imaging device positioned adjacent the patient "P", imaging device 56 positioned at a distal end of an imaging arm 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates three-dimensional images of the surgical site "S" in real-time from the imaging data and transmits the three-dimensional images to the display device 44 for display.

The user interface 40 also includes input arms or handles 42 which allow a clinician to manipulate the robotic system 10 (e.g., move the linkages 12, the ends 14 of the linkages 12, and/or the tools 20). Each of the input handles 42 is in communication with the processing unit 30 to transmit control signals thereto and to receive feedback signals therefrom. Each of the input handles 42 may include an input device (e.g., input device 60 (FIG. 3) or input device 70 (FIG. 4)) which allow the surgeon to manipulate (e.g., clamp, grasp, fire, open, close, rotate, thrust, slice, etc.) the tools 20 supported at the ends 14 of the linkages 12.

Figure 2:
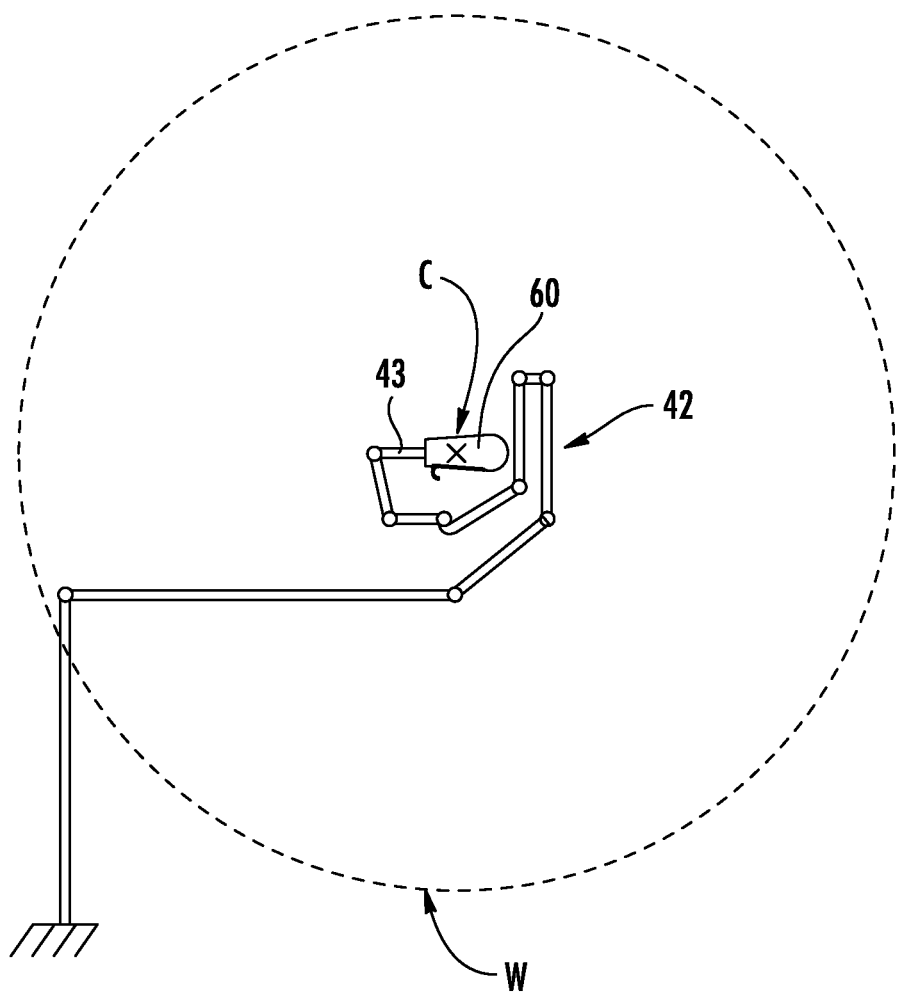
FIG. 2 is a plan view of an arm of the user interface of FIG. 1 within a two-dimensional workspace.

With additional reference to FIG. 2, the input device (e.g., input devices 60 and 70) is moveable through a predefined workspace "W" to move the ends 14 of the linkages 12 within a surgical site "S" or to move the tools 20 that are supported on the ends 14 of the linkages 12. It will be appreciated that while the workspace "W" is shown in two-dimensions in FIG. 2 that the workspace "W" is a three-dimensional workspace. The three-dimensional images on the display device 44 are orientated such that the movement of the input device moves the ends 14 of the linkages 12 as viewed on the display device 44. It will be appreciated that the orientation of the three-dimensional images on the display device may be mirrored or rotated to a view from above the patient "P". In addition, it will be appreciated that the size of the three-dimensional images on the display device 44 may be scaled to be larger or smaller than the actual structures of the surgical site permitting the surgeon to have a better view of structures within the surgical site "S". As the input devices are moved, the tools 20 are moved within the surgical site "S" as detailed below. As detailed herein, movement of the tools 20 may also include movement by the ends 14 of the linkages 12 which support the tools 20.

For a detailed discussion of the construction and operation of a robotic surgical system 1, reference may be made to U.S. Patent Publication No. 2012/0116416, entitled "Medical Workstation."

The movement of the tools 20 is scaled relative to the movement of the input devices (e.g., input devices 60 and 70). The processing unit 30 transmits scaled control signals to the robot base 18 to move the tools 20 in response to the movement of the input handles 42. The processing unit 30 scales the control signals by dividing an Input$_{distance}$ (e.g., the distance moved by one of the input devices) by a scaling factor S$_F$ to arrive at a scaled Output$_{distance}$ (e.g., the distance that one of the ends 14 is moved). In some instances one or more scaling factors "S$_F$" used in operation during a surgical procedure may be in a range between about 1 and about 10 (e.g., 3). This scaling may be represented by the following equation:

$$\text{Output}_{distance} = \text{Input}_{distance}/S_F.$$

It will be appreciated that the larger scaling factor "S$_F$", the smaller the movement of the tools 20 relative to the movement of the input devices. Thus, to facilitate repositioning of the input device relative to a surgical tool 20 driven by the input device, a larger scaling factor "S$_F$" may be used instead so that the tool 20 moves much less than the input device. In some instances this repositioning scaling factor may be at least about 100 or more.

In those instances where the scaling factor is less than one (e.g. operating scaling factor is about 0.5 and repositioning scaling factor is 0.005) then the scaling factor may be multiplied by the input distance to calculate the output distance that the tools are moved.

Figure 3:
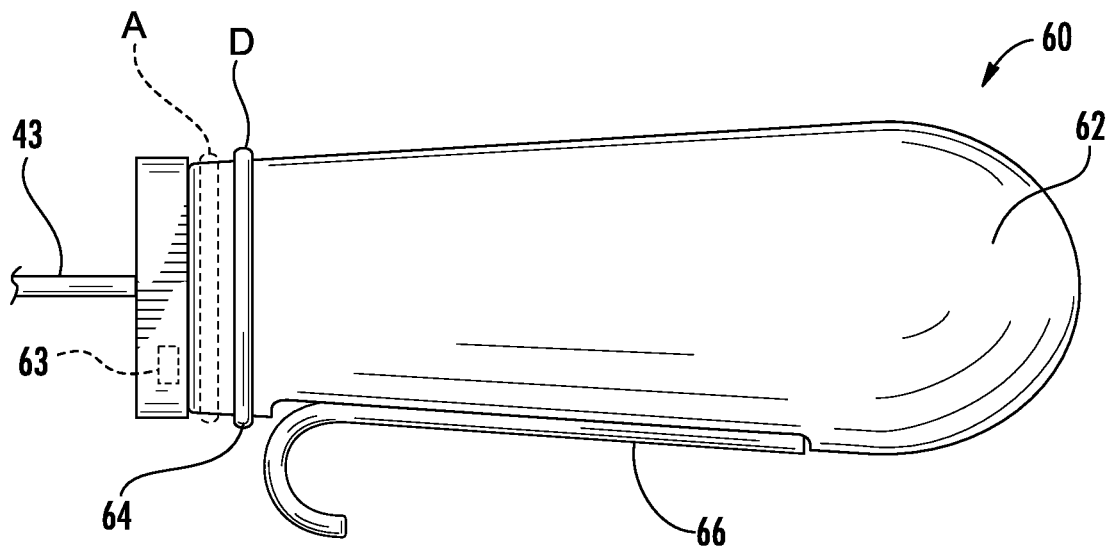
FIG. 3 is a side view of an input device provided in accordance with the present disclosure.
Figure 4:
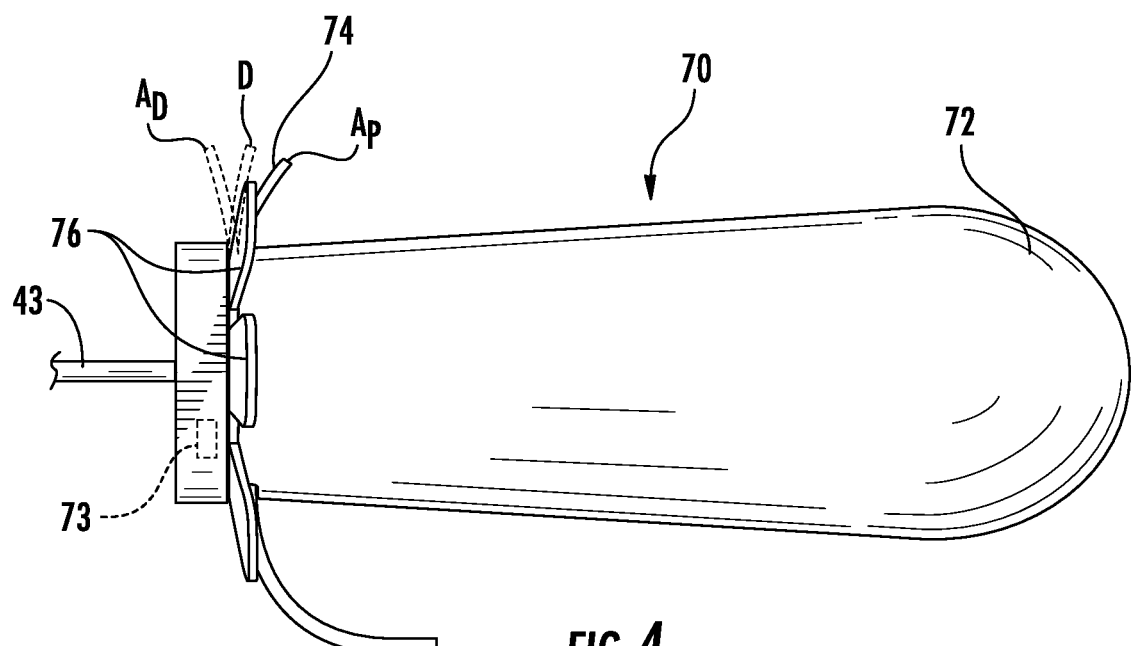
FIG. 4 is side view of another input device provided in accordance with the present disclosure.
Figure 5:
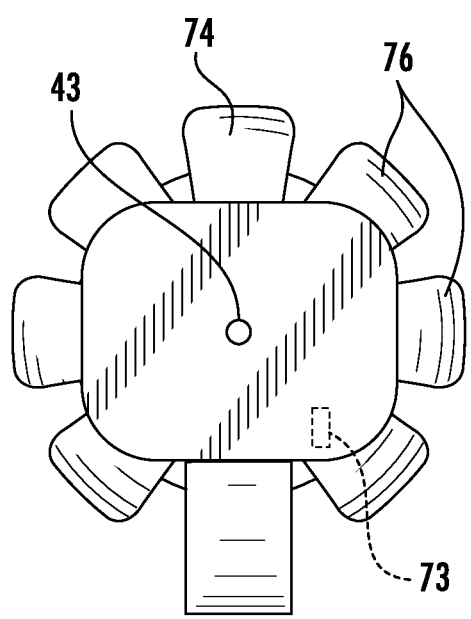
FIG. 5 is an end view of the input device of FIG. 4.

The input devices (e.g., input devices 60 and 70), as shown in FIGS. 3-5, may include a repositioning control (e.g., repositioning controls 64 and 74) that sends a signal to the processing unit 30 to switch the scaling factor "S$_F$" between an operating scaling factor "OS$_F$" used during the surgical procedure and a repositioning scaling factor "RS$_F$" facilitating a repositioning of the input device 60 and/or 70. The operating scaling factor "OS$_F$" may be much smaller than the repositioning scaling factor "RS$_F$" when both scaling factors are greater than one and larger when both scaling factors are less than one. In some instance operating scaling factor "OS$_F$" may be in a range of about 1.0 to about 10.0 (e.g., 3.0) and the repositioning scaling factor "RS$_F$" may be in a range of about 100.0 to about 1000.0 (e.g., 500.0). The two scaling factors allow a clinician to perform a surgical procedure using the operating scaling factor "OS$_F$" and then reposition an input device using the repositioning scaling factor "RS$_F$" when the input device approaches an edge or a limit of movement of the predefined workspace "W" while still keeping the input device fully coupled to the surgical tool. Thus, the clinician may toggle the repositioning control to the activated position "A" to switch to the repositioning scaling factor "RS$_F$" and then move the input device to a desired position within the predefined workspace "W" (adjacent the center "C") while keeping the input device operatively coupled to the tool 20. Once the input device is at the desired position within the predefined workspace "W", the clinician may then toggle the repositioning control to the deactivated position to switch back to a desired operating scaling factor "OS$_F$" and continue the surgical procedure.

"Clutching" the input device 60, 90 from the tool 20 may operatively decouple the tool 20 from the input device 60, 90 so that movement of the input device 60, 90 in at least one predetermined direction does not necessarily result in a corresponding movement of the tool 20. However, during repositioning the input device 60, 90 remains operatively coupled to the tool 20 so that movement of the input device 60, 90 in the predetermined direction results in a corresponding movement of the tool 20 that is lessened by the "repositioning" scaling factor amount instead of the "operating" scaling factor amount used during the surgical procedure. For a more detailed discussion of the clutching and scaling of movement of the linkages 12 of a robotic system 10 in response to movement of the input handles 42, reference may be made to U.S. Patent Application Ser. No. 62/118,123, filed Feb. 19, 2015.

With reference to FIG. 3, the input device 60 is coupled to an input shaft 43 of the input handles 42. The input device 60 is rotatable about the input shaft 43 and may be translatable along a longitudinal axis defined by the input shaft 43. The input device 60 includes a body 62, a controller 63, a repositioning control 64, and input interfaces (e.g., lever 66). The body 62 is ergonomically shaped for engagement by the hand of a clinician. The body 62 may provide a clinician with a tactile feel similar to holding a surgical instrument. The body 62 may also provide tactile feedback (e.g., haptic feedback) to a clinician. The controller 63 is in communication with the processing unit 30 to send signals from the input device 60 to the processing unit 30 to control manipulation of the tools 20 (FIG. 1) of a robotic system 10 in response to manipulation of the body 62, the repositioning control 64, and the input interfaces of the input device 60. It is contemplated that the controller 63 may send the control signals to the processing unit 30 in a wired or wireless manner.

The input interfaces may be specific to a respective tool 20 that is supported at the end 14 of a linkage 12. For example, an input interface or lever 66 of the input device 60 may be for moving a jaw (not shown) of a tool 20. Additionally or alternatively, the lever 66 may be for applying electrosurgical energy to tissue with a tool 20.

Continuing to refer to FIG. 3, the repositioning control 64 is positioned about the body 62 of the input device 60. As detailed above, the repositioning control 64 functions to selectively "repositioning" the manipulation of the input device 60 and/or input interfaces with the tool 20. The repositioning control 64 may be a ring positioned about the body 62 of the input device 60. As shown the repositioning control 64, is positioned between an end of the body 62 that engages the input shaft 43 and the lever 66. It is contemplated, that the repositioning control 64 may be positioned about the other end of the body 62. As so configured, the repositioning control 64 may be activated at any radial location about the input device 60.

The repositioning control 64 may be slidable between a deactivated position "D" and an activated position "A". The repositioning control 64 may be engagable by a clinician and biased towards the deactivated position "D". The biasing of the repositioning control 64 may be calibrated to permit engagement of a finger of a clinician to move the repositioning control 64 to the activated position "A". As shown, to move the repositioning control 64 to the activated position "A", the repositioning control 64 may be moved distally or towards input shaft 43; however, it is contemplated that the orientation of the repositioning control 64 may be reversed such that proximal movement or movement away from the input shaft 43 moves the repositioning control 64 towards the activated position "A". It is also contemplated, that the repositioning control 64 may be rotated about an axis of the body 62 to move the repositioning control 64 towards the activated position "A".

In the deactivated position "D" of the repositioning control 64, the processing unit 30 permits the input device 60 to manipulate the tool 20 in response to manipulation of the input device 60 and the input interfaces. In the activated position "A" of the repositioning control 64, the processing unit 30 may change the scaling factor applied to an input device movement so that the tool 20 moves much less as detailed above.

In other instances, one of the activated and deactivated positions "A", "D" of the repositioning control 64 may be used to enter a traditional "clutching" mode in which the tool 20 is operatively decoupled from the input device 60 so when the input device 60 is moved the tool 20 does not move. The other of the activated and deactivated positions "A", "D" of the repositioning control 64 may be used to leave the "clutching" mode and recouple the input device 70 to the tool 20 so that the tool 20 moves as the input device 70 is moved.

With reference to FIGS. 4 and 5, another input device 70 is provided in accordance with the present disclosure. The input device 70 is similar to the input device 60 detailed above with like elements labeled in a similar manner, as such only the differences will be detailed herein. The input device 70 includes a body 72, a controller 73, and a plurality of petals 74, 76. The body 72 may be squeezable to control the movement of jaws (not shown) of a tool 20 (FIG. 1). Each of the plurality of petals 74, 76 extend away from the body 72 and are spaced apart from one another such that each of the plurality of petals 74, 76 may be selectively engagable. The plurality of petals 74, 76 includes a repositioning petal 74 and input interface petals 76. The repositioning petal 74 may be moveable between a proximal activated position "$A_P$" and a deactivated position "D". The repositioning petal 74 may also have a distal activated position "$A_D$". The proximal and distal activated positions "$A_P$", "$A_D$" of the repositioning petal 74 may be substantially similar to the activated position "A" and deactivated position of the repositioning control 64 detailed above. Additionally or alternatively, one of the activated positions "$A_P$", "$A_D$" of the repositioning petal 74 may change the scaling factor applied from an operating scaling "$OS_F$" used during the surgical procedure to a repositioning scaling factor "$RS_F$", as detailed above, and the other one of the activated positions "$A_P$", "$A_D$" of the repositioning petal may revert the scaling factor back to the previous scaling factor.

In other instances, one of the activated and deactivated positions "$A_P$", "$A_D$" of the repositioning petal 74 may be used to enter a traditional "clutching" mode in which the tool 20 is operatively decoupled from the input device 70 so when the input device 70 is moved the tool 20 does not move. The other of the activated and deactivated positions "$A_P$", "$A_D$" of the repositioning petal 74 may be used to leave the "clutching" mode and recouple the input device 70 to the tool 20 so that the tool 20 moves as the input device 70 is moved.

Figure 6:
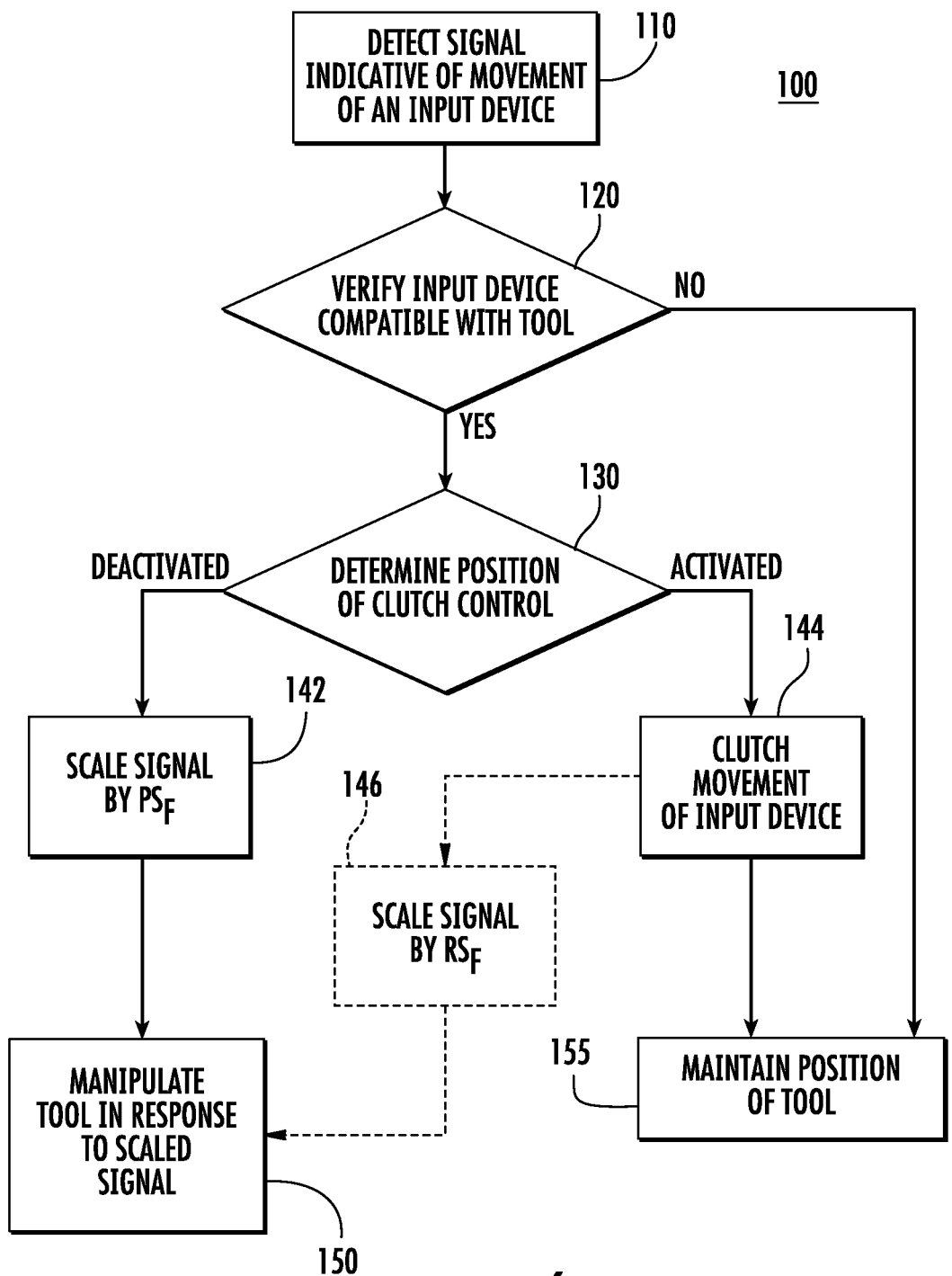
FIG. 6 is a schematic diagram of a method for controlling movement of the robotic surgical system of FIG. 1 in accordance with the present disclosure.

With reference to FIG. 6, a method 100 of controlling a tool 20 of a robotic system 10 with a processing unit 30 in response to movement of input device 60 is disclosed in accordance with the present disclosure. It will be appreciated that method 100 may be used with a variety of other input devices (e.g., input device 70).

The processing unit 30 receives a signal indicative of movement of an input device coupled to an input shaft 43 of an input arm 42 of a robotic surgical system 10 (Step 110). The signal may be from the controller 63 of the input device 60 or from another component of the user interface 40. The processing unit 30 compares the signal from the controller 63 with the identifying information specific to tool 20 attached to the end 14 of the linkage 12 to verify that the input device 60 is compatible with the tool 20 (Step 120). The processing unit 30 may verify the input device 60 is compatible with the tool 20 by comparing a characteristic signal from the tool 20 with the signal from the controller 63. If the processing unit 30 verifies that the input device 60 is compatible with the tool 20, the processing unit 30 determines the position of the repositioning control 64 as detailed below. If the processing unit determines the input device 60 is incompatible with the tool 20, the processing unit 30 maintains the position of the tool 20 in response to signals from the controller 63 (Step 155). Additionally, the processing unit 30 may provide indicia to a clinician if the tool 20 is compatible or incompatible with the input device 60. For example, the processing unit 30 may provide visual indicia on the display device 44 (FIG. 1) or may illuminate the body 62 a distinct color. It is also contemplated that the processing unit 30 may provide audible indicia to a clinician.

Next, the processing unit 30 determines the position of the repositioning control 64 (Step 130). It will be appreciated that the signal from the controller 63 may include data including the position of the repositioning control 64. Additionally or alternatively, the controller 63 may send a separate repositioning control signal to the processing unit 30 to provide the position of the repositioning control 64.

When the repositioning control 64 is in the deactivated position, the processing unit 30 scales the signal from the input device 60 by a first scaling factor (e.g., scaling factor "$S_{F1}$" or operating scaling factor "$OS_F$") (Step 142). Then, the processing unit 30 manipulates the tool 20 in response to the scaled signal (Step 150).

When the repositioning control 64 is in the activated position, the processing unit 30 scales the signal from the input device 60 by a second scaling factor (e.g., scaling factor "$S_{F2}$" or repositioning scaling factor "$RS_F$") (Step 144). Then, the processing unit 30 manipulates the tool 20 in response to the scaled signal (Step 150).

In some instances, if one of the scaling factors is selected to be zero, then the processing unit 30 may maintain the position of the tool 20 as though the tool 20 were communicatively decoupled from the input device 60 until the scaling factor is changed to a non-zero value.

The wireless connections detailed herein (e.g., between controller 63 and the processing unit 30) may be via radio frequency, optical, WIFI, Bluetooth® (an open wireless protocol for exchanging data over short distances (using short length radio waves) from fixed and mobile devices, creating personal area networks (PANs)), ZigBee® (a specification for a suite of high level communication protocols using small, low-power digital radios based on the IEEE 802.15.4-2003 standard for wireless personal area networks (WPANs)), etc.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A method of controlling a tool of a robotic system, the method comprising:

receiving a signal representative of a movement distance of an input device coupled to an input shaft of an input arm;
determining a position of a repositioning control of an input device, wherein the repositioning control is supported on a body of the input device;
scaling the movement distance based on a repositioning scaling factor or an operating scaling factor depending on the position of the repositioning control;
moving the tool of the robotic system based on the scaled movement distance, the tool moving based on the operating scaling factor at least a lesser distance than based on the repositioning scaling factor; and
scaling the movement distance based on the repositioning scaling factor when the repositioning control is in an active position and scaling the movement distance based on the operating scaling factor when the repositioning control is in an inactive position,
wherein the repositioning control of the input device includes a petal extending radially from the body.

2. The method according to claim 1, wherein the repositioning control includes a ring disposed about the body of the input device.

3. The method according to claim 2, further comprising determining that the ring is in the active position when the ring is slid away from a neutral position along a longitudinal axis of the body of the input device and determining that the ring is in the inactive position when the ring is in the neutral position.

4. The method according to claim 3, further comprising determining that the ring is in the active position when the ring is rotated away from a neutral position about a longitudinal axis of the body of the input device and determining that the ring is in the inactive position when the ring is in the neutral position.

5. The method according to claim 1, further comprising determining that the petal is in the active position when the petal is moved away from a neutral position and determining that a ring is in the inactive position when the ring is in the neutral position, wherein engaging the petal of the input device includes pivoting the petal proximally.

6. The method according to claim 5, wherein the petal is moved away from the neutral position when pivoted away from the neutral position.

7. A method of controlling a tool of a robotic system, the method comprising:
receiving a signal representative of a movement distance of an input device coupled to an input shaft of an input arm;
determining a position of a repositioning control of an input device, wherein the repositioning control is supported on a body of the input device;
scaling the movement distance based on a repositioning scaling factor or an operating scaling factor depending on the position of the repositioning control;
moving the tool of the robotic system based on the scaled movement distance, the tool moving at least a lesser distance than based on the repositioning scaling factor; and
scaling the movement distance based on the repositioning scaling factor when the repositioning control is in an active position and scaling the movement distance based on the operating scaling factor when the repositioning control is in an inactive position,
wherein the repositioning control of the input device includes a petal extending radially from the body.

8. The method according to claim 7, wherein the repositioning control includes a ring disposed about the body of the input device.

9. The method according to claim 8, further comprising determining that the ring is in the active position when the ring is slid away from a neutral position along a longitudinal axis of the body of the input device and determining that the ring is in the inactive position when the ring is in the neutral position.

10. The method according to claim 9, further comprising determining that the ring is in the active position when the ring is rotated away from a neutral position about a longitudinal axis of the body of the input device and determining that the ring is in the inactive position when the ring is in the neutral position.

11. The method according to claim 7, further comprising determining that the petal is in the active position when the petal is moved away from a neutral position and determining that a ring is in the inactive position when the ring is in the neutral position, wherein engaging the petal of the input device includes pivoting the petal proximally.

12. The method according to claim 11, wherein the petal is moved away from the neutral position when pivoted away from the neutral position.

13. A method of controlling a tool of a robotic system, the method comprising:
receiving a signal representative of a movement distance of an input device coupled to an input shaft of an input arm;
determining a position of a repositioning control of an input device, wherein the repositioning control is supported on a body of the input device;
scaling the movement distance based on a repositioning scaling factor or an operating scaling factor depending on the determined position of the repositioning control;
moving the tool of the robotic system based on the scaled movement distance, the tool moving at least a lesser distance than based on the repositioning scaling factor; and
scaling the movement distance:
based on the repositioning scaling factor when the repositioning control is in an active position; or
based on the operating scaling factor when the repositioning control is in an inactive position,
wherein the repositioning control of the input device includes a petal extending radially from the body.

14. The method according to claim 13, wherein the repositioning control includes a ring disposed about the body of the input device.

15. The method according to claim 14, further comprising determining that the ring is in the active position when the ring is slid away from a neutral position along a longitudinal axis of the body of the input device and determining that the ring is in the inactive position when the ring is in the neutral position.

16. The method according to claim 15, further comprising determining that the ring is in the active position when the ring is rotated away from a neutral position about a longitudinal axis of the body of the input device and determining that the ring is in the inactive position when the ring is in the neutral position.

17. The method according to claim 13, further comprising determining that the petal is in the active position when the petal is moved away from a neutral position and determining that the ring is in the inactive position when the ring is in the neutral position, wherein engaging the petal of the input device includes pivoting the petal proximally.

18. The method according to claim 17, wherein the petal is moved away from the neutral position when pivoted away from the neutral position.

\* \* \* \* \*